United States Patent [19]

Hochmair et al.

[11] 4,419,995

[45] Dec. 13, 1983

[54] SINGLE CHANNEL AUDITORY STIMULATION SYSTEM

[76] Inventors: Ingeborg J. Hochmair; Erwin S. Hochmair, both of A-1130 Wien Jaunerstrafse 27, Vienna, Austria

[21] Appl. No.: 303,547

[22] Filed: Sep. 18, 1981

[51] Int. Cl.³ ............................................. A61N 1/18
[52] U.S. Cl. .............................. 128/419 R; 128/784; 179/107 R
[58] Field of Search ..................... 128/419 R, 421–423, 128/784, 786, 789; 179/107 R, 107 BC, 107 F

[56] References Cited

U.S. PATENT DOCUMENTS

| | | | |
|---|---|---|---|
| 2,995,633 | 8/1961 | Puharich | 179/107 R |
| 3,384,090 | 5/1968 | Manfredi | 128/422 |
| 3,752,939 | 8/1973 | Barty | 128/1 R X |
| 4,063,048 | 12/1977 | Kissiah, Jr. | 179/107 R |

OTHER PUBLICATIONS

Freese, "An Implant Pierces Walls of Deafness", Parade, Jun.10, 1979, pp. 20-22.

Dillier et al., "A Computer Controlled Test System...", Scand. Audiol. Suppl. 11 (1980), pp. 163-170.

Douek et al., "A New Approach to the Cochlear Implant", Proc. Roy. Soc. Med., vol. 70, Jun. 1977, pp. 379-383.

Primary Examiner—Lee S. Cohen
Attorney, Agent, or Firm—Flehr, Hohbach, Test, Albritton & Herbert

[57] ABSTRACT

Chronic auditory stimulation is achieved by establishing an electric field at the base of the cochlea whereby full speech patterns are imparted to a patient. Penetration of the cochlea is not required thereby reducing the risks in installing the implanted electrodes. In a preferred embodiment the electrodes are disc shaped with the ground electrode being larger than the active electrode. The active electrode is preferably placed in the round window at the base of the cochlea or on the promontory. The ground electrode is placed 2-10 mm from the active electrode to thereby confine the electric field. The interconnections to the electrodes are tissue compatible insulation covered wires thereby minimizing stimulation of cutaneous nerve fibers.

19 Claims, 5 Drawing Figures

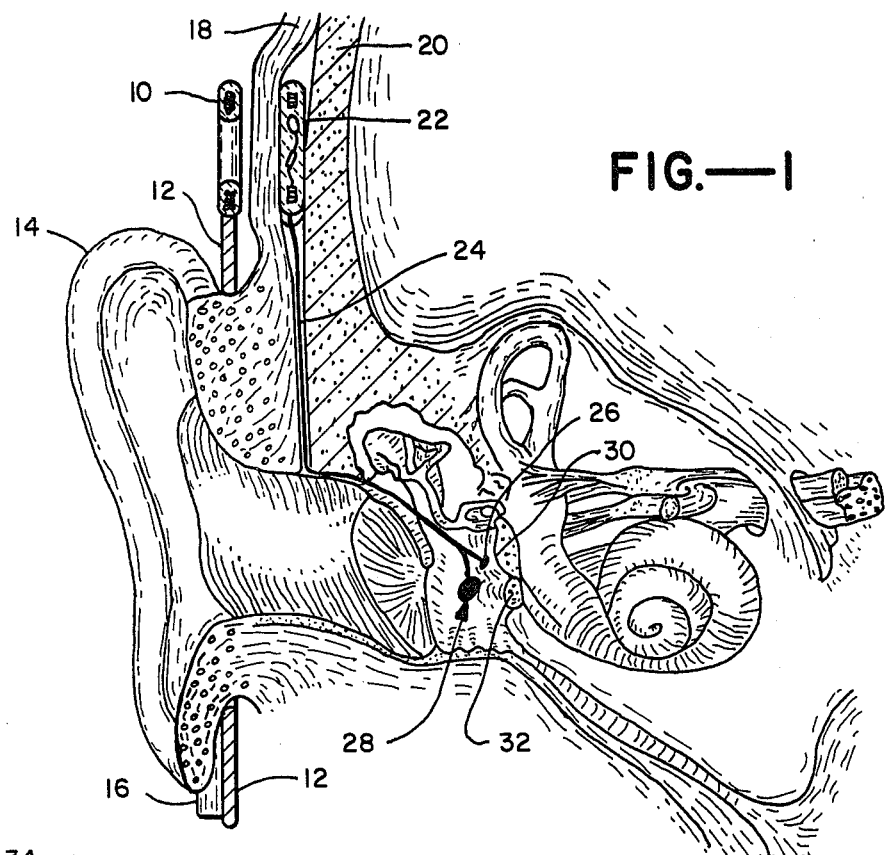
FIG.—1
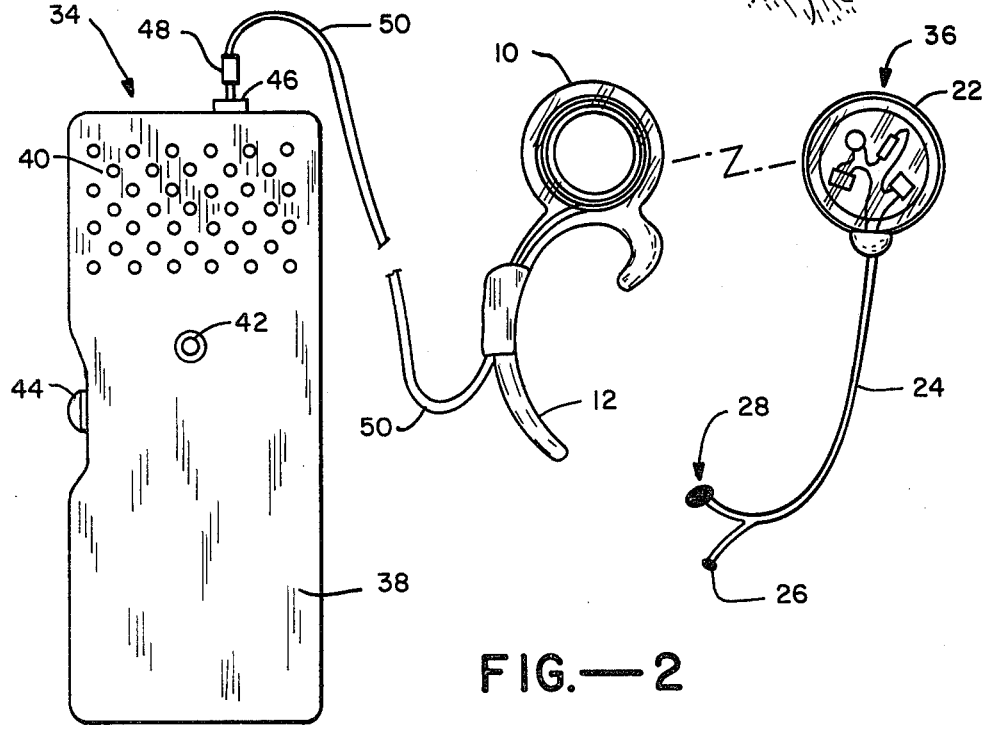
FIG.—2

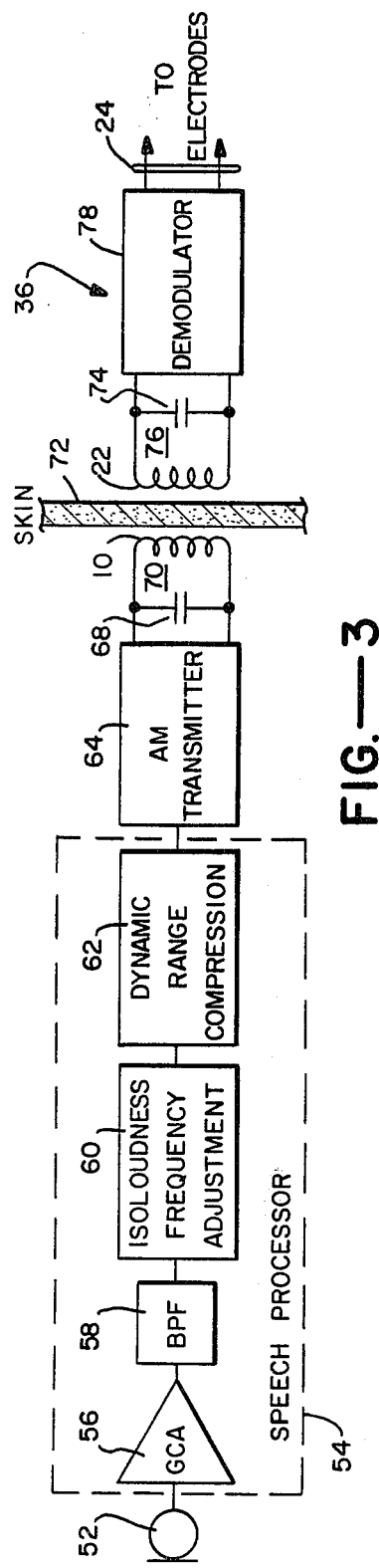
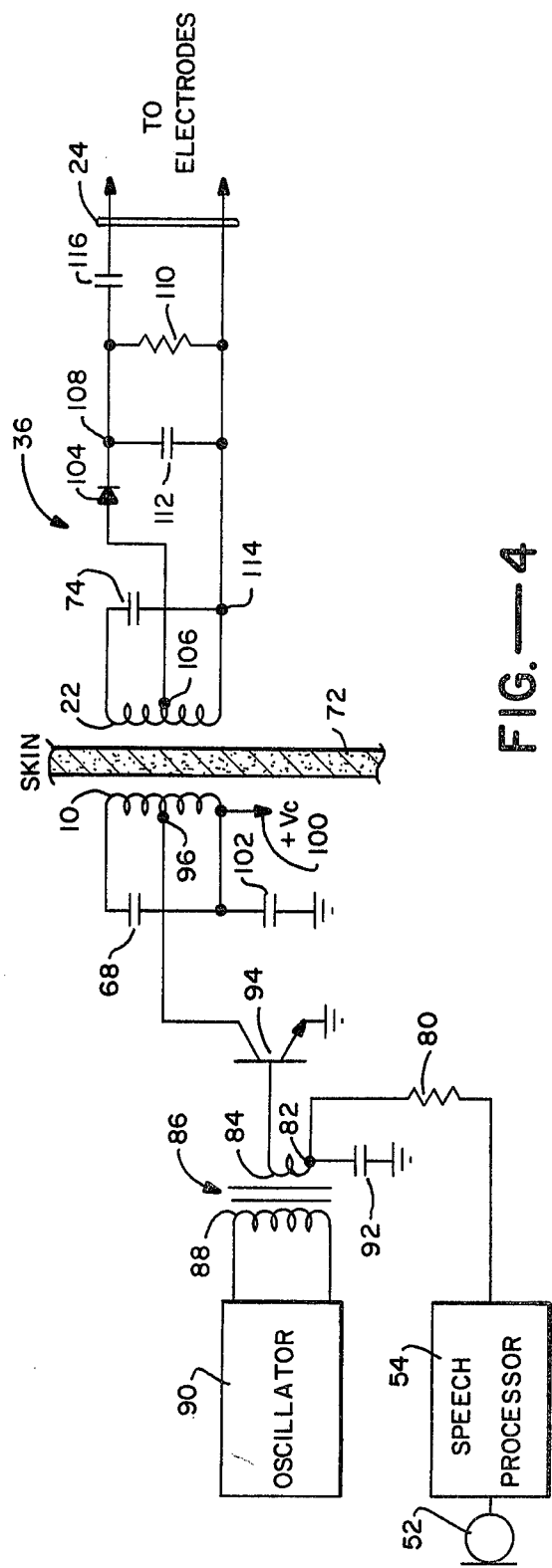

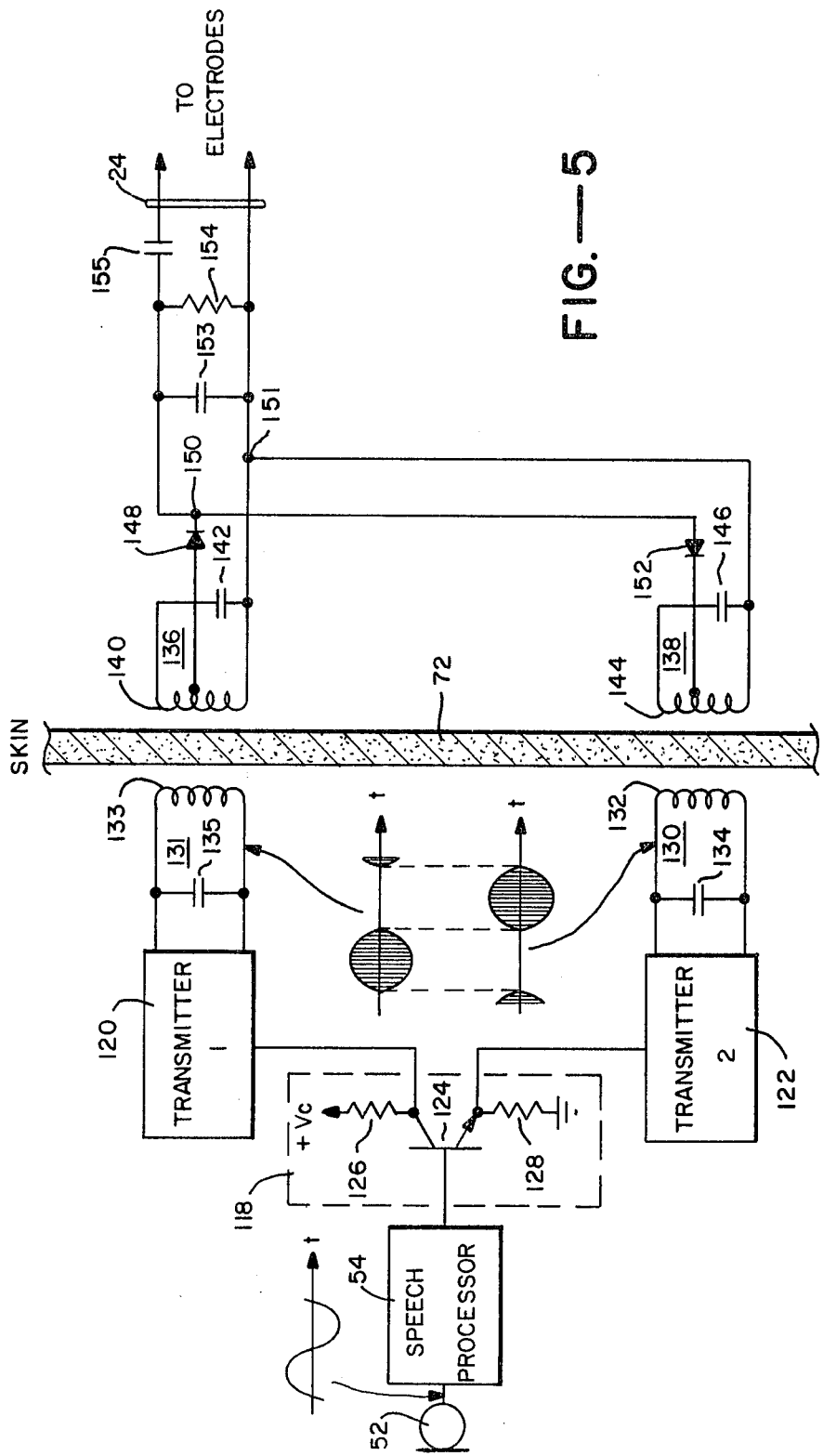
FIG.—5

SINGLE CHANNEL AUDITORY STIMULATION SYSTEM

This invention relates generally to apparatus for neural and muscle stimulation such as for facilitating hearing in the deaf, and more particularly the invention relates to a method and means for stimulating by means of electrical signals.

The use of subcutaneously implanted hearing devices is known. U.S. Pat. No. 3,209,081 discloses a device which is implanted in the mastoid bone. The receiver makes direct contact with the bone through which sound waves may be conducted to the inner ear.

More recently, implanted prosthetic devices for stimulating the auditory nerve by means of electrical pulses have been disclosed. U.S. Pat. No. 3,449,768 discloses the use of coded pulse trains to create an electrical gradient field to facilitate visual or audio stimulations. U.S. Pat. No. 3,752,929 discloses the use of an electrode including a pair of elongated conductors for implanting in the cochlea.

Schindler et al, "Multielectrode Intracochlear Implants" Arch Otolaryngol, Vol. 103, December 1977, discloses the use of spatial excitation of the cochlear nerve in cats. Clark and Hallworth, "A Multiple-Electrode Array for Cochlear Implant", J. Laryngol, Otol, 90/7, 1976 discloses a ribbon array including a plurality of elongated flat electrodes which are positioned along the length of the cochlea for stimulating the auditory nerve. Similarly, bundles of thin wires have been employed by the Stanford Auditory prosthesis group by direct placement into the auditory nerve.

In our U.S. Pat. No. 4,284,856 and our co-pending application Ser. No. 267,405, filed May 26, 1981, a multi-channel auditory stimulation system is disclosed wherein selected cochlea excitation is achieved by using a multi-electrode prosthetic device which is inserted in the scala tympani of the cochlea. Different tones can be perceived by the patient through selective excitation of the cochlea with the multi-electrode prosthetic device.

However, the necessary implantation of the multi-electrode prosthesis entails some risk and inevitably destroys residual hair cells which are the basic sensory units in the inner ear. Accordingly, the procedure is not recommended for deaf children. Moreover, where ossification of the inner ear has occurred, the prosthetic device cannot be inserted into the cochlea.

The positioning of an electrode outside of the cochlea for electrical stimulation of the chochlea nerve has been proposed for experimental testing purposes. However, such experiments have caused pain in the patients and the stimulation of the electrode is limited to frequencies below 500 hertz and only limited speech pattern components were involved. Moreover, the tests have been for limited periods of time with the electrodes thereafter being removed from the patient.

An object of the present invention is an improved auditory stimulation system for chronic hearing enhancement.

Another object of the invention is an auditory stimulation system which can be more easily inserted in a patient.

Still another object of the invention is a method of cochlea stimulation without the requirement for physical placement of an electrode in the cochlea.

Briefly, in accordance with the invention an auditory stimulation system comprises a single channel signal transmitter which can be carried on a person and a single channel receiver which is subcutaneously implanted in a patient. The receiver includes a plurality of electrodes which are positioned in close proximity to the base of the cochlea.

In a preferred embodiment a pair of electrodes are employed with the active electrode being generally disc shaped with a diameter of approximately 1.5 to 2 millimeters. A ground electrode is equal to or greater in size than the active electrode and is positioned on the order of 2 to 10 millimeters from the active electrode. Accordingly, a small electric field can be generated which is effective in stimulating the cochlea nerve without also stimulating other nerve fibers. Wires interconnecting the electrodes are covered by a suitable insulation to prevent excitation of cutaneous nerve fibers. Preferably, the active electrode is placed in the round window at the base of the cochlea or on the promontory bone.

In operation the electrodes may be energized by electrical signals in a frequency band of sufficient width to impart complete speech patterns and without the patient experiencing pain or other discomforts at the higher frequencies. The frequency band signal is continuous over the frequency band and is no limited to frequency components.

The invention and objects and features thereof will be more readily apparent from the following detailed description and appended claims when taken with the drawings, in which:

FIG. 1 is a cross sectional view showing the physiological aspects of the human ear and the disposition of the stimulation apparatus of the present invention.

FIG. 2 illustrates the physical configuration of the signal processor, the transmitter, and the implantable receiver modules.

FIG. 3 is a block diagram of a stimulation apparatus in accordance with the present invention.

FIG. 4 is an electrical schematic diagram of a transmitter and receiver network of the block background of FIG. 2.

FIG. 5 is an electrical schematic of an alternative configuration of a transmitter and receiver combination.

Referring first to FIG. 1, there is shown a cross-sectional view illustrating the external and internal structures of the ear. The present invention comprises an external transmitter which is arranged to provide an AM modulated carrier signal to a transmitter coil 10, the coil being disposed upon a molded plastic earhook member 12 which is adapted to be clipped to the auricle 14. As will be more fully explained hereinbelow, the transmitter itself may conveniently be packaged in a container which may be worn by or carried by the patient, with flexible leads coupling the output of the transmitter module to the coil 10 on the earhook. Alternatively, using well-known micro-miniaturization techniques, the transmitter electronics may be so packaged so as to also fit on the earhook 12 with the result that only very short leads are required to couple the transmitter output to the transmitting coil 10. In this regard, in FIG. 1, the transmitter module 16 is illustrated as being affixed to the earhook member 12.

Surgically implanted between the temporal muscle 18 and the skull bone 20 is an implanted receiver module 22. The earhook 12 and its coil 10 are designed such that when the earhook is disposed on the auricle 14, the coil 10 of the transmitter is generally aligned axially and laterally with the receiving coil of the implant 22. Coupled between the output of the receiver module 22 and the tissue to be stimulated, is an insulated lead 24, having a stimulating tip electrode 26 at its distal end, as well as a ground or indifferent electrode 28. The lead 24 is preferably routed between the tissue defining the external acoustic meatus and the skull bone so as to avoid the necessity of penetrating the tympanic membrane. More particularly, the surgical installation of the implant begins with an arch-shaped retro-auricular incision. After lifting the periosteum, a delve is milled into the temporal bone, and the receiver module, which is generally disc shaped, is positioned inside the delve and secured to the bone with fibrinogenous glue and sutures. The lead wires 24 connecting the receiver module to the electrode surfaces are also positioned within a milled bone-canal up to the external ear canal. Next, the tympanic membrane is put forward and a groove is milled into the back wall of the ear canal to protect the electrode. The subiculum is milled down and it thus becomes possible to approach the round window membrane or the promontory. Following the positioning and attachment of the electrode surfaces to the particular location to be stimulated, the tympanic membrane is repositioned and the auditory canal is camponated. The lead 24 thus enters the cavity of the middle ear and the active electrode 26 is suitably affixed to near the base of the cochlea such as to either the promontory bone 30 or to the round window membrane 32.

As can best be seen in FIG. 2, the active electrode 26 may comprise a small bead or disc formed on the end of the insulated wire lead 24 and may have a diameter of, for example, 1.5 to 2.0 millimeters. The ground or indifferent electrode 28 is arranged to be positioned within the middle ear, approximately 2-10 mm from the active electrode 26 and is preferably approximately two to three times larger in area than the active electrode 26. In this fashion, the current density at the site of the active electrode is several times greater than at the site of the indifferent electrode, ensuring that the stimulation is focused at the point of contact of the active electrode 26.

With reference to FIG. 2, the apparatus of the present invention is shown to comprise an external unit indicated generally by numeral 34 and an implantable unit indicated generally by numeral 36. The external unit comprises a housing 38 which may be located in a wearer's pocket and which is arranged to contain a microphone element (not shown) disposed in the area of the housing 38 in which perforations 40 are formed. In this fashion, sound waves may reach the microphone. Also contained within the housing 38 is a battery supply and the transmitter and signal processing electronics yet to be described. An LED 42 may be provided to indicate battery status. Further, a thumbwheel switch/control 44 can be used to turn the external unit on and off and, if desired, to vary parameters such as the gain of the amplifiers used in the signal processing electronics. The output voltage of the speech processor unit can also be varied. Disposed on the top end of the housing 38 is a jack 46 adapted to receive a standard plug 48 such that the output from the transmitter may be coupled via conductors 50 to the transmitting coil 10 formed on the ear hook member 12.

The implant 36 comprises a round wafer-like portion in which the receiving coil 22 is disposed. Within the central opening of the annular coil 22 are the electrical components comprising the receiver electronics. The coil and electrical components are imbedded in a suitable body-compatible plastic such as Silastic, Teflon or the like, and the receiver is encased in a hermetic fluid-tight enclosure. The receiver's output is developed across the active electrode tip 26 and the ground or indifferent electrode 28. The electrical conductors leading from the wafer portion of the implant to the electrode surfaces are encased in an insulating biocompatible sheath.

Preferably, the conductor portion of the lead terminating at the active electrode 26 is fabricated of a material exhibiting a spring action whereby during implantation, the lead may be bowed or flexed so that the ball or disc electrode surface 26 may be positively urged against the body structure to be stimulated i.e., the promontory or the round window membrane. Alternatively, where promontory stimulation is involved, a small recess may be drilled into the promontory bone to receive the active electrode and a suitable adhesive may be used to hold the electrode in position. Consider now the electrical construction of the invention with reference to the embodiments of FIGS. 3-5. FIG. 3 is a block diagram of the system. Microphone 52 generates an electrical output which is applied to the speech processor electronics shown as being enclosed by the broken line box 54. Included in the speech processor channel is a gain controlled amplifier 56 which receives as its input the electrical output from the microphone 52 and the output from the grain control amplifier 56 is applied through a band-pass filter 58 to a so-called isoloudness frequency adjustment circuit 60. The speech processor electronics 54 further includes a dynamic range compression circuit 62 which may either precede or follow the isoloudness frequency adjustment circuit 60.

The construction and operation of the speech processor electronics 54 is fully set forth and described in our co-pending application Ser. No. 267,405, filed May 26, 1981.

The output from the speech processor 54 is arranged to modulate the output from an RF oscillator in the AM transmitter module 64. The modulated output from the transmitter is applied across a transmitting coil 66 and a capacitor 68, these last mentioned two components being designed to cooperate as a tuned circuit 70.

The implant unit 36 is shown to the right of the skin interface 72 and includes the receiver coil 22 and parallel capacitor 74 which form a tuned receiver circuit 76. The output from the tuned receiver circuit is coupled as an input to a diode demodulator network 78 which functions in a conventional fashion to remove the modulation envelope from the RF carrier. The output from the diode demodulator is applied via the leads 24 to the active and indifferent electrode surfaces.

FIG. 4 is an electrical schematic of the AM transmitter module 64. In this figure, the microphone pick-up 52 and the speech processor module 54 connected to it are connected through a resistor 80 to a first terminal 82 of the secondary winding 84 of a transformer indicated generally by numeral 86. The primary winding 88 of the transformer is coupled across the output of an RF oscillator 90. The terminal 82 has an RF decoupling capacitor 92 connected between it and ground. The other terminal of the secondary winding 84 is connected directly to the base electrodes of an NPN transistor 94. The emitter contact of the transistor is connected to ground and the collector contact is tied to a center tap terminal 96 of a transmitting coil 66. A capacitor 68 is connected directly in parallel with the entire transmitting coil 66 and the requisite DC bias voltage for the transistor 94 is applied at terminal 100. A further RF decoupling capacitor 102 is connected between ground and the common junction of the coil 10 and the capacitor 68.

The implanted receiver module 36 comprises a receiving coil 22 and a tuning capacitor 74 connected in parallel. The demodulator portion of the receiver comprises a semiconductor diode 104 having an anode connected to a center-tap terminal 106 on the receiving coil 22 and a cathode electrode connected to a junction point 108. A resistor 110 and a capacitor 112 are connected in parallel between the junction point 108 and the terminal 114 of the coil 22. A blocking capacitor 116 is disposed in series between the junction point 108 and the active electrode. The ground or indifferent electrode is tied directly to the terminal 114.

In operation, the modulation signal which is a speech derived, time varying wave, originates at the output of the speech processor 54 and is applied to the transistor modulator via resistor 80 as is the RF carrier from the oscillator 90 via the transformer coupled to the base of the transistor 94. The capacitor 92 as well as the capacitor 102 serve to decouple the RF signal from the DC supply. The collector of the modulation transistor 94 is connected to the tap of the tuned transmitter circuit which includes the coil 10 and the capacitor 68. The transmitter coil 10 inductively couples the modulated carrier signal to the implanted receiver coil 22 which, together with the capacitor 74, also comprises a tuned receiver circuit. The received signal is demodulated by the semiconductor diode 104 with capacitor 112 providing RF decoupling and resistor 110 providing the requisite DC path to ground. The capacitor 116 serves to block any DC current from reaching the electrodes.

Importantly, by placing the electrodes near the base of the cochlea such as on the round window membrane or on the promontory, a concentrated electrical field is established which responds to the amplitude and frequency of the transmitted speech signal which a patient can perceive and understand speech.

It will be noted that the modulation signal from the speech processor 54 in FIG. 4 is applied to the base of the output transistor 94 by way of the transformer's secondary winding 84. By introducing the modulation signal on the base electrode, output transistor saturation is avoided. Where collector modulation is employed, however, this undesirable saturation could result. It is feasible, however, to introduce the modulation signal at the emitter electrode.

An alternative arrangement of an external speech processor and transmitter combination and an implantable receiver combination is illustrated in FIG. 5. Here, a single speech processor network 54 and a single set of stimulating electrodes are interfaced with a dual transmission channel for performing transcutaneous stimulation. The microphone pick-up 52 provides its output to the speech processor 54 which, again, may be configured as set forth in the aforereferenced application Ser. No. 267,405. The modulation signal from the speech processor network 54 is applied to a phase splitter indicated generally by numeral 118 and from there to AM transmitters 120 and 122. The phase splitter is shown as including NPN transistor 124 having its collector electrode connected through a resistor 126 to a source of potential $V_c$ and the emitter electrode connected through a resistor 128 to ground. The signal derived from the collector electrode of the transistor 124 is applied to the transmitter 120 while the signal appearing at the emitter electrode of transistor 124 is applied to the transmitter 122.

Transmitter 120 delivers its output to a tuned circuit 131 comprised of the transmitter coil 133 and parallel capacitor 135 while transmitter 122 provides its output to a similar tuned circuit 130 comprised of a transmitter coil 132 and a tuning capacitor 134. Implanted beneath the temporal muscle posterior to the patient's auricle is a receiver module including tuned circuits 136 and 138 which are inductively coupled to the transmitting tuned circuits 131 and 130, respectively. The tuned circuit 136 includes a receiving coil 140 and an associated tuning capacitor 142 while the tuned circuit 138 includes a receiving coil 144 and its associated tuning capacitor 146. The receiving coil 140 has an intermediate terminal and connected to that terminal is the anode electrode of a semiconductor diode 148. The cathode electrode of that diode is tied to a junction 150. An oppositely poled diode 152 is tied between the junction 150 and an intermediate terminal on the receiver coil 144. The lowermost terminals of the receiving coils 140 and 144 are tied together at a junction point 151. Connected between the junction points 150 and 151 is a parallel combination of an RF bypass capacitor 153 and a load resistor 154. The junction 150 is also coupled through a DC blocking capacitor 155 to the active electrode while the junction 151 is connected to the ground or indifferent electrode.

The arrangement shown in FIG. 5 is used to stimulate only one particular site (the promontory or round window membrane) using the two electrodes of a single channel. However, it uses two transmission channels arranged to operate in a push-pull configuration. The advantage of using this push-pull arrangement is that the resistor 154 may be made very large (or even deleted) such that substantially all of the power transmitted to the implant reaches the electrode, neglecting of course the diode losses. It is thus possible to reduce input power by about a factor of four as compared to the single transmission channel device of FIG. 4.

The embodiment shown in FIG. 5 may be thought of as comprising two transmission channels, each being essentially equivalent to the single transmission channel of FIG. 4, cooperatively driving a single receiver channel. With resistor 154 having a large value as compared to the electrode impedance, it will absorb any differential dc current resulting from any asymmetry in the transmission characteristics of the two transmission channels. It offers the further advantage in that it may function in the same fashion as the resistor 110 in FIG. 4 should only one transmission channel be operative. Thus, this configuration increases reliability by offering an additional transmission channel in case one transmission channel is lost, albeit at a lower efficiency.

Those skilled in the art will recognize that instead of constructing the band-pass filter using two tuned parallel resonant circuits as in the embodiment of FIGS. 4 and 5, it is also possible to implement the band-pass filter with one series tuned circuit and one parallel tuned circuit. In such a case, the input of the band-pass filter should not be current driven, but rather voltage driven, in order to obtain a relative maximum of the induced voltage at the point of critical coupling. In the arrangement where the series tuned circuit forms a part of the transmitter, the output transistor preferably works in the saturated condition and may be modulated by collector modulation. Where the series tuned circuit forms a part of the receiver electronics, however, the parallel tuned circuit of the transmitter should be driven by a non-saturated RF amplified.

The invention has proved successful in improving a patient's perception capabilities and in providing understanding of speech. Since the installation of the electrode does not require penetration into the cochlea, the risks involved are reduced and damage to the hair cells of the cochlea is obviated. Sufficiently large dynamic ranges have been found up to approximately 10K Hz. The upper limit of stimulation strength is caused by too loud of a sensation and not by pain. A wide frequency range (e.g. 50–3500 Hz) for a full speech pattern can be accommodated without inducing pain or other deleterious effects in the patient.

While the invention has been described with reference to specific embodiments, the description is illustrative and not to be construed as limiting the invention. Various modifications and applications may occur to those skilled in the art without departing from the true spirit and scope of the invention.

We claim:

1. A method of chronic auditory stimulation of the cochlea for imparting speech patterns comprising the steps of placing an active electrode and a ground electrode outside of and near the base of a cochlea of a patient, and energizing said electrodes with an electrical signal having a frequency band which is sufficient to define a speech pattern thereby establishing an electric field between said active electrode and said ground electrode.

2. The method as defined by claim 1 wherein said active electrode is placed in proximity to the round window at the base of the cochlea.

3. The method as defined by claim 1 wherein said active electrode is placed on the promontory bone.

4. A method of chronic auditory stimulation of the cochlea for imparting speech patterns comprising the steps of generating a first signal having predetermined amplitude and frequency dependent components corresponding to speech patterns,
    transmitting said first signal to a subcutaneously implanted receiver, and
    applying said first signal as received by said receiver to a pair of spaced electrodes positioned outside of the cochlea whereby an electrical field is established for stimulating the cochlea in response to said speech patterns.

5. The method as defined by claim 4 wherein said step of transmitting comprises modulating a carrier signal by said first signal and coupling the modulated carrier signal to said receiver.

6. The method as defined by claim 4 wherein said pair of electrodes includes an active electrode which is positioned near the round window at the base of the cochlea.

7. The method as defined by claim 4 wherein said pair of electrodes includes an active electrode which is positioned on the promontory bone.

8. A system for chronic auditory stimulation comprising
    transmission means for generating and transmitting a frequency band signal having predetermined amplitude and frequency dependent characteristics corresponding to speech signals,
    receiver means for receiving said frequency band signal,
    a plurality of electrodes configured for positioning outside of the cochlea for establishing an electric field near the base of the cochlea, and
    interconnection means connecting said receiver means and said plurality of electrodes whereby said electrodes respond to said frequency band signal and establish an electrical field for stimulating the cochlea in response to speech signals.

9. A system as defined by claim 8 wherein said plurality of electrodes includes an active electrode and a ground electrode.

10. A system as defined by claim 9 wherein said active electrode is configured for placement in proximity to the round window at the base of the cochlea.

11. The system as defined by claim 9 wherein said active electrode and ground electrode are disc shaped.

12. A system as defined by claim 9 wherein said ground electrode is larger than said active electrode.

13. A system as defined by claim 8 wherein said transmission means comprises a single channel amplitude modulation transmitter.

14. A system as defined by claim 13 wherein said receiver means comprises a passive single channel amplitude modulation receiver.

15. A system as defined by claim 8 wherein said transmission means further includes pickup means for receiving sound waves including substantially the entire range of speech frequencies and producing electrical signals corresponding to said sound waves, speech processing means coupled to said pickup means for receiving said electrical signals and converting said electrical signals to a modulation signal having predetermined frequency and amplitude dependent characteristics, transmitter means coupled to receive said modulation signal and producing a radio frequency carrier signal which is modulated in accordance with said modulation signal, and means for inductively coupling the output from said transmitter means to said receiver means.

16. The system as defined by claim 15 wherein said receiver means is arranged for subcutaneous implantation at a predetermined location within the patient and includes demodulator means for recovering said modulation signal from said modulated carrier signal.

17. The system as defined by claim 8 or 16 wherein said interconnection means comprises tissue compatible insulation covered wires.

18. The system as defined by claim 17 wherein said wires exhibit a springlike property whereby one of said electrodes is urged into position at the base of the cochlea.

19. The system as defined by claim 8 wherein said frequency band signal includes the frequency range of 50 Hz to 3.5 kHz.

* * * * *